US00PP14815P3

(12) United States Plant Patent
Bentley

(10) Patent No.: US PP14,815 P3
(45) Date of Patent: May 25, 2004

(54) *GAURA LINDHEIMERI* PLANT NAMED 'COLSO'

(50) Latin Name: *Gaura lindheimeri*
Varietal Denomination: Colso

(75) Inventor: Howard Bentley, Victoria (AU)

(73) Assignee: Pride of Place Plants, Sidney (CA)

( * ) Notice: Subject to any disclaimer, the term of this patent is extended or adjusted under 35 U.S.C. 154(b) by 0 days.

(21) Appl. No.: 10/160,952

(22) Filed: May 30, 2002

(65) Prior Publication Data

US 2003/0226183 P1 Dec. 4, 2003

(51) Int. Cl.[7] ..... A01H 5/00

(52) U.S. Cl. ..... Plt./226

(58) Field of Search ..... Plt./226

*Primary Examiner*—Kent Bell

(74) *Attorney, Agent, or Firm*—Christie, Parker & Hale, LLP

(57) ABSTRACT

A new variety of *Gaura lindheimeri* plant named 'Colso' that is characterized by yellow-white marginal leaf variegation with a central leaf color of green and petal color of red to red-purple.

2 Drawing Sheets

Classification: The present invention relates to a new *Gaura lindheimeri* plant.

Variety denomination: The new plant has the varietal denomination 'Colso'.

BACKGROUND OF THE INVENTION

The present invention relates to a new and distinct variety of Gaura having attractive variegated foliage. The new cultivar is known botanically as *Gaura lindheimeri* and will be referred to hereinafter by the variety name 'Colso'.

'Colso' is a naturally occurring branch mutation discovered in a controlled planting of *Gaura lindheimeri* 'Siskiyou Pink' (unpatented).

Asexual reproduction of the new cultivar was first accomplished using softwood cuttings in a propagation nursery at Wonga Park, Victoria, Australia. Since that time, through successive generations, the characteristics of the new variety have been determined stable and reproduced true to type.

SUMMARY OF THE INVENTION

The following traits in combination distinguish the 'Colso' variety from all other commercial varieties known to the inventor. 'Colso' has not been tested under all possible conditions and phenotypic differences may be observed with variations in environmental, climatic and cultural conditions.

1. *Gaura lindheimeri* 'Colso' exhibits marginal leaf variegation.
2. *Gaura lindheimeri* 'Colso' exhibits yellow-white variegation color.
3. *Gaura lindheimeri* 'Colso' exhibits red to red-purple petal color.

COMPARISON WITH PARENT

'Colso' is distinguishable from the parent by its variegated foliage.

In comparison, the plant most similar to 'Colso' is *Gaura lindheimeri* 'Jo Adela' (unpatented). 'Colso' differs from this variety in red to red-purple petal color whereas *Gaura lindheimeri* 'Jo Adela' has white petals. In comparison to the co-pending patent application 'Benso' (U.S. plant application Ser. No. 10/160,976) and 'Crimson Butterflies' (U.S. Plant Pat. No. 13,189), although both have the same parent, neither have variegated foliage like 'Colso'.

BRIEF DESCRIPTION OF THE DRAWINGS

The accompanying illustrations depict plants of the new variety in color as true as possible in color photographic illustrations of this nature.

BOTANICAL DESCRIPTION OF THE PLANT

Figure 1:
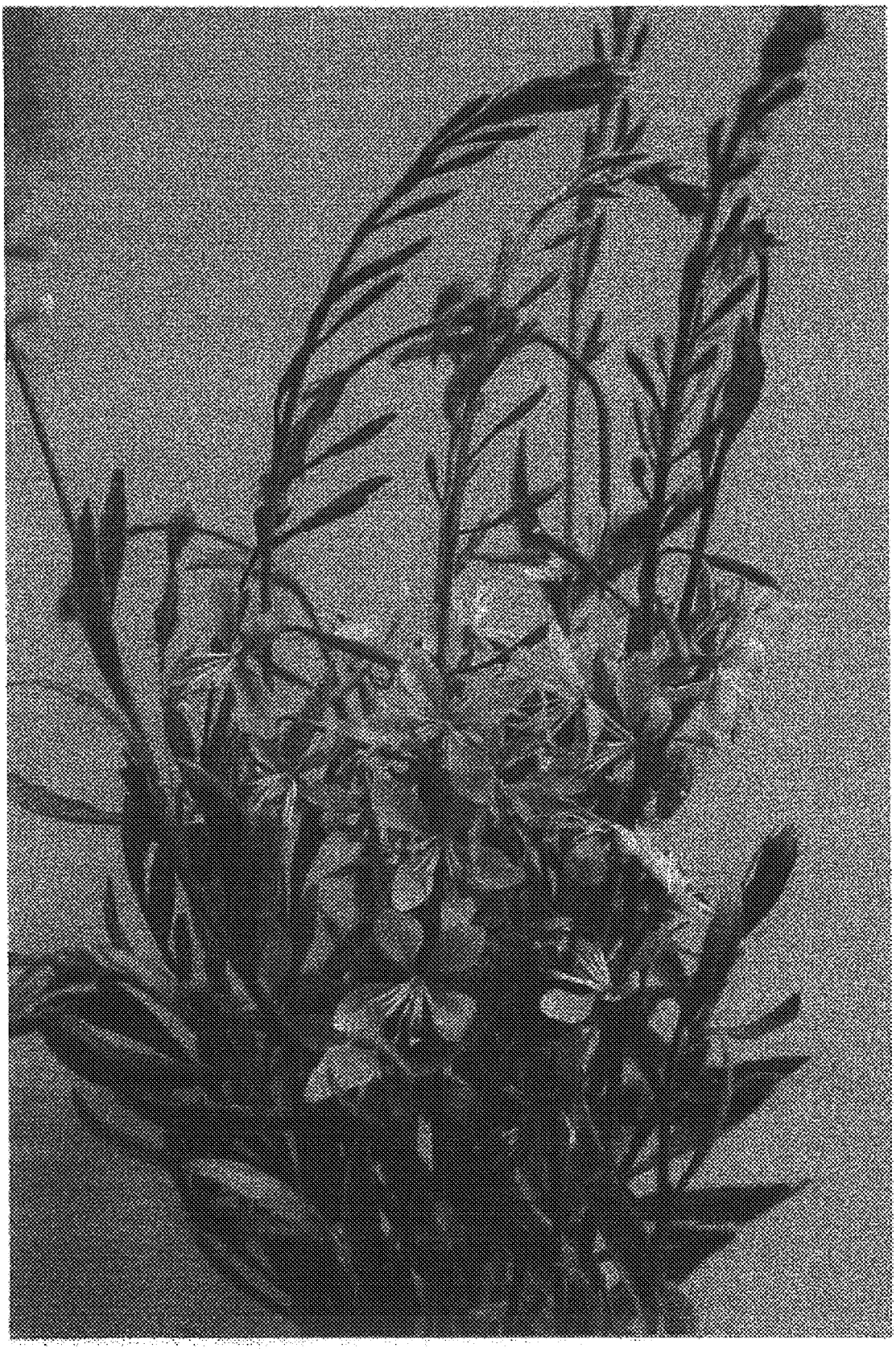
FIG. 1 shows the plant of the new variety.
Figure 2:
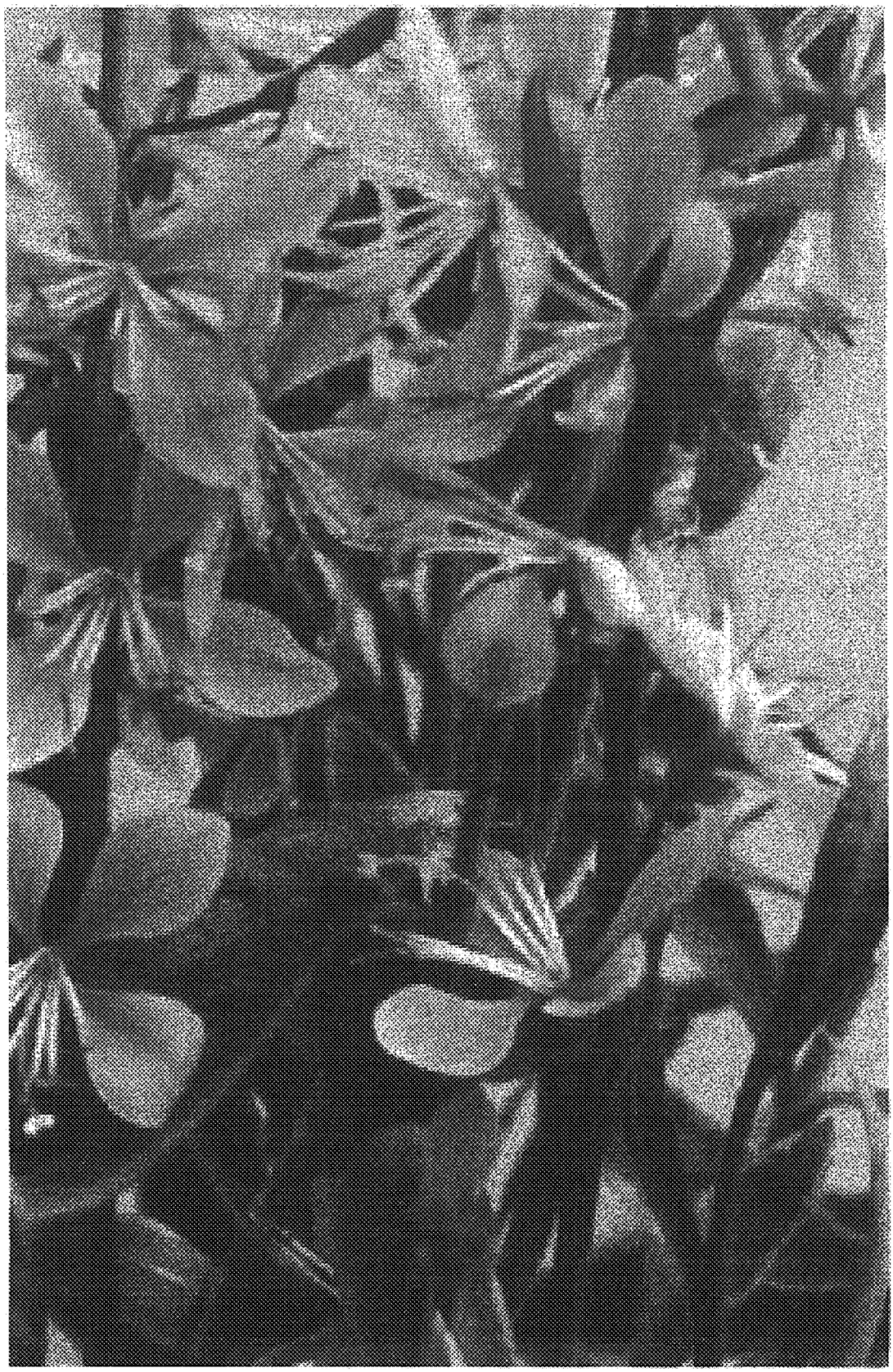
FIG. 2 shows a close up of the flower and variegated foliage of the new variety.

The following is a description of the new variety 'Colso'. Data was collected from plants grown in outdoor conditions, 9 months of age, in flower at Wonga Park, Victoria, Australia. The color determinations are in accordance with the 1995 Edition of The Royal Horticultural Society Colour Chart ("R.H.S.C."), London, England, except where general color terms of ordinary dictionary significance are used.

The plant grows in a spreading habit with medium sparse, vigorous growth, attaining medium height. The growing requirements are similar to other Gaura.

Plant description:

*Commercial classification.*—Perennial.

*Bloom period.*—Spring and summer, extending into fall in Wonga Park, Victoria, Australia.

*Plant habit.*—Spreading mound-shape.

*Height.*—About 75 cm at maturity.

*Width.*—About 90 cm at maturity.

*Hardiness.*—USDA Zone 5 to 10.

*Propagation.*—Propagation is accomplished using vegetative cuttings.

*Time to develop roots.*—About 10 to 14 days, when rooted on a heated bench.

*Crop time.*—About 12 to 14 weeks to produce a 14 cm container plant size with flower from a rooted cutting.

*Disease resistance.*—Generally disease resistant, susceptible to two-spotted mite.

*Stem.*—Shape: Cylindrical. Color: 137B to 137C.

*Dimensions.*—About 50 cm in length and about 0.4 cm in diameter (max dimensions).

*Surface.*—Pubescent with whitish hairs up to about 0.5 mm in length.

*Basal stem color.*—Near to 199A.

*Branching.*—Basal branching. Some lateral branching from upper stem nodes once flowering is initiated.

*Internode length.*—About 1.2 to 1.7 cm between nodes.

*Branching habit.*—Basal branching with spreading stems.

Foliage:

*Shape.*—Linear to lanceolate.

*Apex.*—Acute.

*Base.*—Attenuate.

*Venation.*—Reticulate.

*Vein color* (*adaxial surfaces*).—Near 146C.

*Vein color* (*abaxial surfaces*).—Near 146C.

*Margins.*—Slightly undulate.

*Arrangement.*—Alternate.

*Attachment.*—Sessile.

*Surfaces* (*adaxial and abaxial*).—Finely pubescent to glabrous.

*Mature leaf dimensions.*—Mature leaf dimensions range from about 6 to 8 cm in length and about 1.2 to 1.5 cm in width.

*Leaf color* (*adaxial surface*).—Both colors 137C and 158A are individually present on each individual leaf. 137C is the color of the center and 158A is the variegated margin color.

*Leaf color* (*abaxial surface*).—Both colors 137C and 158A are individually present on each individual leaf. 137C is the color of the center and 158A is the variegated margin color.

*Petiole.*—None.

*Stipules.*—None.

Flowers:

*Inflorescence.*—Raceme.

*Dimensions of inflorescence.*—About 30 cm to 35 cm in length and about 6 cm in diameter (at maturity).

*Flower dimensions.*—About 3 cm in height and about 3 cm in width.

*Total number of flowers per raceme.*—About 30 to 40 flowers per raceme.

*Persistent or self-cleaning.*—Self-cleaning.

*Aspect.*—Facing horizontally.

*Sexuality.*—Bisexual.

*Bud.*—Dimensions: About 0.3 cm in width 2.2 to 2.5 cm in length. Shape: Linear. Color: Buds that are completely closed are the color 185B.

*Flower color* (*adaxial surfaces*).—Pale color of outer edge of petals is near 55B, petal center is near 57C.

*Flower color* (*abaxial surfaces*).—Pale color of outer edge of petals is near 55B, petal center is near 57C.

*Petals.*—Two upper and three lower. Shape: Elliptic. Apex: Acute. Base: Cuneate. Fused or Unfused: Unfused. Dimensions: About 0.9 cm in width and about 1.6 cm in length. Margin: Entire. Surface: Glabrous.

*Calyx.*—Dimensions: About 1.6 cm in length and about 0.5 cm in diameter. Surface: Pubescent.

*Sepals.*—Four in number. Fused or Unfused: Fused. Partially separate once petals are fully open. Surface: Pubescent.

*Peduncle.*—Dimensions: About 10 cm to 15 cm in length and about 2 mm in width. Surface: Pubescent.

*Flower fragrance.*—Flowers have no fragrance.

Reproductive organs:

*Stamens.*—Eight in number. Color: Near 155C. Dimensions: About 1.3 cm in length and about 0.50 mm in diameter.

*Anther.*—Dimensions: About 2.5 mm in length and about 0.5 mm in width. Color: Near 187A. Shape: Linear.

*Pollen.*—Present. Amount: Moderate amount. Color: Near 10A.

*Pistil.*—One. Dimensions: About 1.5 cm in length and about 0.50 mm in width. Color: About 57C.

*Ovary.*—Position: Inferior. Color: Near 187A. Shape: Linear to elliptic. Dimensions: About 8 mm in length and about 1.5 mm in diameter.

*Seed production.*—Seed production has not been observed to date.

I claim:

1. A new and distinct cultivar of *Gaura lindheimeri* plant named 'Colso' substantially as shown and described.

* * * * *